United States Patent [19]

Timgren

[11] Patent Number: 4,696,798

[45] Date of Patent: Sep. 29, 1987

[54] CUVETTE SET FOR BLOOD ANALYSIS

[75] Inventor: Carl J. Timgren, Helsinki, Finland

[73] Assignee: Perlos Oy, Nurmijarvi, Finland

[21] Appl. No.: 827,276

[22] Filed: Feb. 6, 1986

[30] Foreign Application Priority Data

Mar. 6, 1985 [FI]  Finland .................................. 850890

[51] Int. Cl.$^4$ ...................... B29C 45/14; G01N 21/03
[52] U.S. Cl. .................................. 422/102; 264/251;
264/273; 264/297.2; 356/246
[58] Field of Search ...................... 422/58, 65, 66, 102,
422/104; 436/44, 47; 356/246; 264/259, 273,
328.1, 297.2, 251

[56] References Cited

U.S. PATENT DOCUMENTS 3,544,272 12/1970 Vaills ..................................... 422/65
3,699,348 10/1972 Höcherl ................................. 422/65
4,043,678 8/1977 Farrell et al. ........................ 422/102
4,549,742 10/1985 Husak et al. ......................... 264/273

FOREIGN PATENT DOCUMENTS 8300296 2/1983 PCT Int'l Appl. ................... 422/66

Primary Examiner—Barry S. Richman
Assistant Examiner—C. M. Delahunty
Attorney, Agent, or Firm—Pearne, Gordon, McCoy & Granger

[57] ABSTRACT

A cuvette set for blood analysis, comprising a carrier and guide band (2) for fixing the bottom parts of cuvettes (1) so as to build a row of cuvettes parallel to the band, said carrier and guide band (2) being provided with fastening means, such as holes (5) for a control device which carries the row of cuvettes through an analyzer. In order to produce a dimensionally accurate structure, said carrier and guide band (2) is made of a metal and it is provided with fastening means, such as holes (4) for engaging parts (3) protruding from the bottom of plastic cuvettes (1).

8 Claims, 3 Drawing Figures

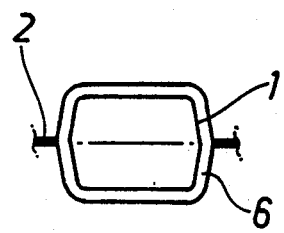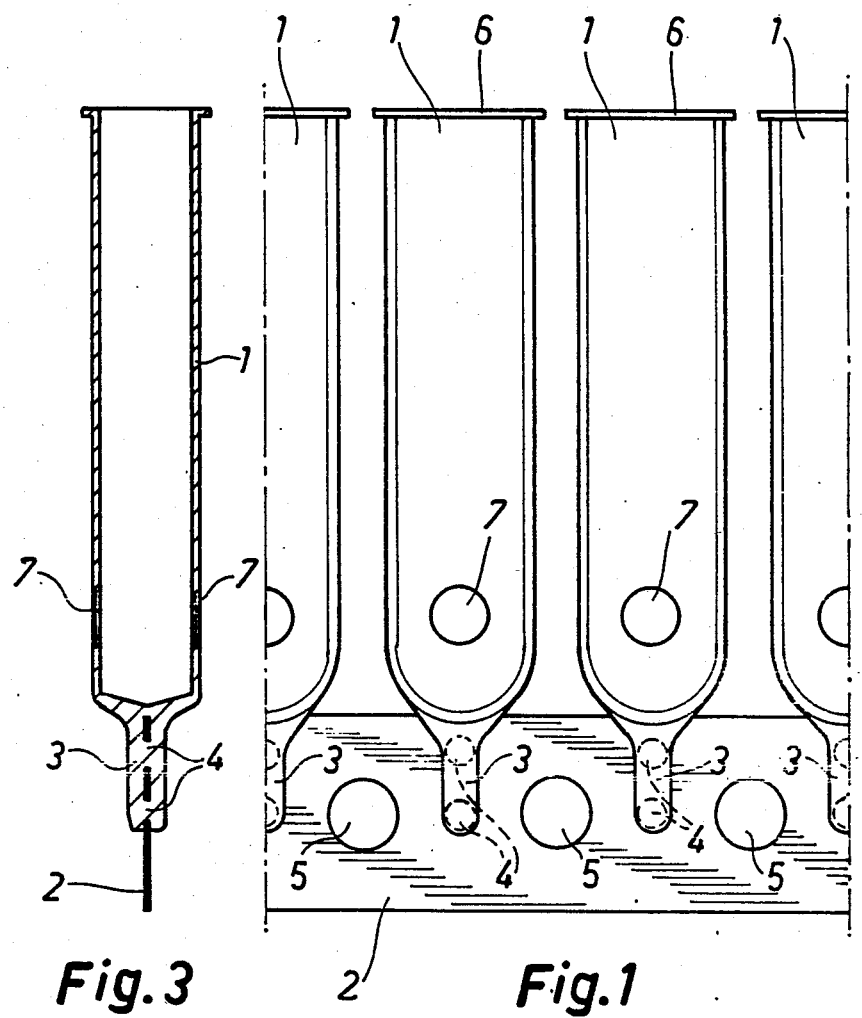

CUVETTE SET FOR BLOOD ANALYSIS

The present invention relates to a cuvette set for blood analysis, comprising a carrier and guide band for fixing the bottom parts of cuvettes so as to build a row of cuvettes parallel to the band, said carrier and guide band being provided with fastening means, such as fastening holes for a control device which carries the row of cuvettes through an analyzer.

Such cuvette sets for blood analysis have been manufactured earlier by making a carrier and guide band of the same plastic film material as cuvettes. A two-layer plastic film is provided by deep drawing technique with a groove corresponding to a cuvette half and these plastic film strips are welded to each other. The plastic film edge remaining below the bottoms of the cuvettes are provided with holes for fastening an analyzer control device. However, this prior art cuvette set design involves several drawbacks. First of all, the dimensional accuracy of such a structure is unsatisfactory in many respects. Due to the extensibility of plastic material when subjected to loading and its high thermal expansion coefficient, the diameter and relative distance of fastening holes vary. Also in vertical direction there are dimensional changes both in terms of the disposition of fastening holes and the height of cuvettes. Also, the distance between window sections intended for the radioscopy of cuvettes is difficult to maintain sufficiently constant. In order to maintain high optical transparency, a selected plastic film should be relatively thin, which however results in the loss of dimensional stability of a cuvette set structure and the increase of the abovementioned dimensional inaccuracies.

All these drawbacks can be eliminated with a cuvette set of the invention for blood analysis, which set is characterized in that a carrier and guide band is made of a material different to cuvettes, the band material being a metal or some other rigid, stable material and said band being provided with fastening means, such as holes for engaging the parts protruding from the bottom of plastic cuvettes.

This type of cuvette set can be manufactured very advantageously with a method of the invention, characterized in that a metal band is perforated and the perforated metal band is placed in a cuvette injection mould or moulds so that a protrusion, which is formed at the bottom of each cuvette and is integral with the cuvette, extends on either side of the metal band and into the fastening holes in the metal band.

It will be appreciated that a cuvette set of the invention for blood analysis is more economical in its manufacturing and material costs than the prior art cuvette set while, at the same time, eliminating all the above drawbacks relating to poor dimensional accuracy and lack of sufficient dimensional stability.

A manufacturing technique of the invention also makes it possible to produce a flange with a flat top surface around the mouth of each cuvette. The flange can be useful when sealing a blood sample containing cuvette with an adhesive tape fastened on top of the flange. In the above-described prior art, cuvettes were sealed by welding the walls of the mouth of a cuvette to each other, which is inconvenient and may damage the cuvettes or samples.

By providing both side faces or wall portions of a cuvette with thinnings or areas of reduced thickness, which are in register with each other and serve as windows for the beam of an analyzer, the rest of a cuvette can be made of a relatively thick material.

Another advantage offered by the invention is that no broken cuvettes are formed in the manufacturing and cuvettes also withstand manipulation and handling so as to remain intact.

One embodiment of the invention will now be illustrated with reference made to the accompanying drawings, in which FIG. 1 is a side view of a cuvette set of the invention for blood analysis and FIG. 2 shows the same in plan view at a single cuvette.

FIG. 3 shows one cuvette in a cuvette set in cross-section.

A cuvette set shown in the drawings is manufactured as follows. First produced is a carrier and guide band 2, in which are made fastening holes 5 for an analyzer control device. Since band 2 is made separately and of a material different to cuvettes, the material for band 2 can be selected in view of the rigidity and stability required thereof. The band 2 is preferably made of a metal but certain types of plastics can also be used. By virtue of a dimensional stability of metal band 2, the diameter and disposition of holes 5 can be determined with high accuracy. This accuracy remains also in subsequent operation, since the forces of an analyzer control device or applied temperatures do not cause notable deformations in metal band 2.

In the section between holes 5 are punched two adjacent holes 4 which act as fastening holes for cuvettes to be manufactured at a later stage. It is obvious that the shape and position of holes 4 and 5 may vary and they can be replaced by recesses, impressions or the like fastening means.

Each cuvette includes a first set of opposed side wall portions located on opposite sides of a first central plane of the cuvette. As shown in FIG. 3, the first central cuvette plane corresponds with a central plane of the band 2 and the opposed cuvette walls are substantially parallel to the plane of the band. For convenience, the cuvette may be considered to have a second central plane which is substantially perpendicular to the first central cuvette plane and a second set of opposed side wall portions located on opposite sides of the second central plane of the cuvette.

Cuvettes 1 are manufactured in an injection mould which may include mould cavities for one or more cuvettes. Metal band 2 is placed in an injection mould so that holes 4 will be in register with a part 3 protruding from the bottom of cuvette 1. When the cuvettes are then injection moulded, said protrusion 3, which is integral with or of the same material as the cuvette, extends on either side of metal band 2 and into said fastening holes 4 in the metal band.

Since cuvettes are manufactured with injection moulding technique, said cuvettes can be given any desired shape. In the present case, the mouth of a cuvette is surrounded by a flange 6, which has a flat top surface and which is useful in sealing the cuvette by means of an adhesive tape fastened on top of flange 6.

By using separately movable, compressible mould sections, it is possible to provide the side faces or wall portions of a cuvette wtih thinnings or areas of reduced thickness 7, serving as optical windows for the beam of an analyzer.

I claim:

1. A cuvette set for blood analysis, comprising a plurality of plastic cuvettes molded onto a carrier and guide band, each of said cuvettes including a bottom wall portion extending to first and second sets of opposed side wall portions, the side wall portions of said first set being located on opposite sides of a first central plane of the cuvette and the side wall portions of said second set being located on opposite sides of a second central plane of the cuvette, said first central plane being essentially perpendicular to said second central plane, and an integral protrusion extending below the bottom wall portioon of the cuvette, said band comprising a strip of rigid material different from the plastic material forming said cuvettes and having two opposed flat surfaces located on opposite sides of a central plane of the strip of material, said band being located below the bottom wall portions of the cuvettes with said central plane of the strip of material being substantially parallel to said first central plane of the cuvettes, each of said protrusions extending along at least one of said flat surfaces of the band and being rigidly fixed to the band by first fastening means to accurately position said cuvettes with respect to said band, said band including second fastening means constructed and arranged to engage a control device to carry the band and cuvettes through an analyzer with the cuvettes in a proper position for analysis of samples contained therein.

2. A cuvette set for blood analysis as set forth in claim 1, wherein said first and second sets of opposed side wall portions of each of said plurality of plastic cuvettes define a mouth and wherein a flange with a flat top surface is formed on said first and second sets of side walls surrounding said mouth.

3. A cuvette set for blood analysis as set forth in claim 1, wherein each of said first set of opposed side wall portions includes a region of reduced wall thickness in register with each other to serve as windows.

4. A method for the manufacture of a cuvette set for blood analysis as set forth in claim 1, comprising the steps of providing a molding chamber constructed and arranged for molding at least one of said cuvettes of said cuvette set onto said carrier and guide band positioned therein, providing a plurality of first perforations extending through said band for cooperating with said protrusions to form said first fastening means, providing a plurality of second perforations extending through said band to form said second fastening means, positioning said band in said molding chamber with said first perforations positioned in and in register with that part of said molding chamber at which an associated one of said protrusions is to be formed adjacent the bottom of said cuvettes, injecting a plastic material into said molding chamber to form said cuvettes, with said protrusions including an integral portion thereof extending into said first perforations, and removing said cuvettes and band from the molding chamber.

5. A method for the manufacture of a cuvette set for blood analysis as set forth in claim 4, wherein said first and second sets of opposed side wall portions cooperate to define a cuvette mouth at an end of each cuvette of said cuvette set opposite the respective bottom wall portion of the cuvette and said molding chamber includes means for forming a flange around the mouth of each cuvette, said flange having a flat top surface.

6. A method for the manufacture of a cuvette set for blood analysis as set forth in claim 4, wherein before injection of said plastic material separately moveable and compressible mold sections are positioned in said molding chamber to form opposed regions of reduced wall thickness in each of said set of first side wall portions in register with each other to serve as windows.

7. A method for the manufacture of a cuvette set for blood analysis as set forth in claim 4, wherein each of said protrusions is molded along both of said flat surfaces of said band and through said associated one of said first perforations.

8. A cuvette set for blood analysis comprising a plurality of cuvettes formed of a plastic material molded onto a carrier and guide band, each of said cuvettes including a bottom wall portion extending to first and second sets of opposed side wall portions, the side wall portions of said first set being located on opposite sides of a first central plane of the cuvette and the side wall portions of said second set being located on oposite sides of a second central plane of the cuvette, said first central plane being essentially perpendicular to said second central plane, and an integral protrusion extending below the bottom wall portion of the cuvette, said band comprising a strip of metal having opposed flat surfaces located on opposite sides of a central plane of the strip, said band including a plurality of first and second perforations extending therethrough, said band being located below the bottom wall portions of the cuvettes with said central plane of the metal strip having a fixed substantially parallel orientation with respect to said first central plane of the cuvette, each of said protrusions extending along both of said flat surfaces of the band and through at least one associated first perforation to rigidly fix and accurately position the cuvettes with respect to the band, said second perforations being constructed and arranged to engage a control device to carry the band and cuvettes through an analyzer with the cuvettes in a proper position for analysis of samples contained therein.

* * * * *